US011083568B2

(12) United States Patent
Nguyen et al.

(10) Patent No.: US 11,083,568 B2
(45) Date of Patent: Aug. 10, 2021

(54) INTRAOCULAR LENS INSERTER CARTRIDGE WITH AN IOL-GUIDING STRUCTURE

(71) Applicant: RxSight, Inc., Aliso Viejo, CA (US)

(72) Inventors: Hoang Nguyen, Anaheim, CA (US); Ilya Goldshleger, Ladera Ranch, CA (US)

(73) Assignee: RxSight, Inc., Aliso Viejo, CA (US)

( * ) Notice: Subject to any disclaimer, the term of this patent is extended or adjusted under 35 U.S.C. 154(b) by 150 days.

(21) Appl. No.: 15/426,059

(22) Filed: Feb. 7, 2017

(65) Prior Publication Data
US 2018/0221142 A1 Aug. 9, 2018

(51) Int. Cl.
*A61F 2/14* (2006.01)
*A61F 2/16* (2006.01)

(52) U.S. Cl.
CPC .......... *A61F 2/1678* (2013.01); *A61F 2/1667* (2013.01)

(58) Field of Classification Search
CPC ...... A61F 2/1662; A61F 2/1667; A61F 2/167; A61F 2/1672; A61F 2/1678; A61F 2/1675; A61F 2002/1681; A61F 2002/1682; A61F 2002/16903; A61F 2002/16905; A61F 2002/169051; A61F 2002/169052; A61F 2002/169053; A61F 2/1691
See application file for complete search history.

(56) References Cited

U.S. PATENT DOCUMENTS

| 5,474,562 | A |   | 12/1995 | Orchowski et al. |              |
|-----------|---|---|---------|------------------|--------------|
| 5,499,987 | A | * | 3/1996  | Feingold         | A61F 2/1664  |
|           |   |   |         |                  | 206/5.1      |
| 5,653,753 | A | * | 8/1997  | Brady            | A61F 2/1664  |
|           |   |   |         |                  | 606/107      |
| 5,800,442 | A | * | 9/1998  | Wolf             | A61F 2/167   |
|           |   |   |         |                  | 606/107      |
| 5,803,925 | A | * | 9/1998  | Yang             | A61F 2/1664  |
|           |   |   |         |                  | 606/107      |

(Continued)

FOREIGN PATENT DOCUMENTS

| EP | 1625834 A2   | 2/2006 |
| EP | 2 939 637 A1 | 4/2015 |

(Continued)

OTHER PUBLICATIONS https://www.thefreedictionary.com/groove, retrieved Aug. 7, 2019, definition of the term "groove" (Year: 2019).*

*Primary Examiner* — Erich G Herbermann

(57) ABSTRACT

A cartridge of an intraocular lens inserter comprises an insertion nozzle, having a distal insertion channel; an intraocular lens (IOL)-folding stage, to receive and to fold an IOL, proximal to the insertion nozzle, and having a proximal insertion channel; and an IOL-guiding structure. The IOL-guiding structure can include a first proximal guiding groove, or a first proximal guiding rib, or both, formed in the IOL-folding stage. An intraocular lens inserter comprises an inserter cylinder; a push-rod, partially in the inserter cylinder; a cartridge-receiving insertion end, to receive a cartridge that includes an insertion nozzle, having a distal insertion channel; an IOL-folding stage, proximal to the insertion nozzle, having a proximal insertion channel; and an IOL-guiding structure.

14 Claims, 11 Drawing Sheets

(56) References Cited

U.S. PATENT DOCUMENTS

| | | | |
|---|---|---|---|
| 5,876,440 A * | 3/1999 | Feingold | A61F 2/1664 128/898 |
| 5,947,975 A * | 9/1999 | Kikuchi | A61F 2/1664 606/107 |
| 6,001,107 A * | 12/1999 | Feingold | A61F 2/1664 206/5.1 |
| 6,129,733 A | 10/2000 | Brady et al. | |
| 6,206,887 B1 * | 3/2001 | McDonald | A61F 2/1691 606/107 |
| 6,248,111 B1 * | 6/2001 | Glick | A61F 2/1675 606/107 |
| 6,283,975 B1 * | 9/2001 | Glick | A61F 2/1675 606/107 |
| 6,355,046 B2 | 3/2002 | Kikuchi et al. | |
| 6,447,520 B1 | 9/2002 | Ott et al. | |
| 6,554,839 B2 * | 4/2003 | Brady | A61F 2/1664 606/107 |
| 6,712,848 B1 | 3/2004 | Wolf et al. | |
| 6,723,104 B2 | 4/2004 | Ott | |
| 6,733,507 B2 * | 5/2004 | McNicholas | A61F 2/1678 606/107 |
| 8,535,331 B2 | 9/2013 | Vaquero et al. | |
| 8,551,165 B2 | 10/2013 | Hohl | |
| 8,668,734 B2 | 3/2014 | Hildebrand et al. | |
| 9,044,317 B2 | 6/2015 | Hlidebrand et al. | |
| 2002/0193805 A1 * | 12/2002 | Ott | A61F 2/1678 606/107 |
| 2003/0050646 A1 * | 3/2003 | Kikuchi | A61F 2/167 606/107 |
| 2003/0176870 A1 * | 9/2003 | Ott | A61F 2/167 606/107 |
| 2003/0195522 A1 | 10/2003 | Mcnicholas et al. | |
| 2004/0087963 A1 | 5/2004 | Ossipov et al. | |
| 2004/0199174 A1 * | 10/2004 | Herberger | A61F 2/1678 606/107 |
| 2004/0267359 A1 * | 12/2004 | Makker | A61F 2/1664 623/6.12 |
| 2005/0065534 A1 * | 3/2005 | Hohl | A61F 2/1678 606/107 |
| 2005/0149058 A1 * | 7/2005 | Lin | A61F 2/167 606/107 |
| 2006/0036262 A1 * | 2/2006 | Hohl | A61F 2/1664 606/107 |
| 2006/0167466 A1 | 7/2006 | Dusek | |
| 2006/0271063 A1 | 11/2006 | Sunada et al. | |
| 2008/0039862 A1 | 2/2008 | Tran | |
| 2008/0200922 A1 | 8/2008 | Brown | |
| 2008/0221585 A1 | 9/2008 | Downer | |
| 2008/0281333 A1 * | 11/2008 | Pessing | A61F 2/1678 606/107 |
| 2011/0015644 A1 * | 1/2011 | Pankin | A61F 2/1678 606/107 |
| 2012/0130390 A1 * | 5/2012 | Davies | A61F 2/1691 606/107 |
| 2013/0165943 A1 | 6/2013 | Downer | |
| 2014/0066946 A1 | 3/2014 | Aguilera et al. | |
| 2014/0303636 A1 * | 10/2014 | Valle | A61F 9/007 606/107 |
| 2016/0250069 A1 * | 9/2016 | Dockhom | A61F 9/0017 606/107 |
| 2018/0271647 A1 * | 9/2018 | Mueller | A61F 2/1678 |

FOREIGN PATENT DOCUMENTS

| | | | |
|---|---|---|---|
| EP | 2 868 295 A1 | 5/2015 | |
| EP | 3 391 855 A1 | 10/2018 | |
| JP | 05103803 A | 4/1993 | |
| JP | 05103808 A | 4/1993 | |
| JP | 05103809 A | 4/1993 | |
| WO | WO 2013/038689 A1 | 3/2013 | |
| WO | WO-2015075489 A2 * | 5/2015 | A61F 2/167 |
| WO | WO 2017/104690 A1 | 6/2017 | |

* cited by examiner

INTRAOCULAR LENS INSERTER CARTRIDGE WITH AN IOL-GUIDING STRUCTURE

TECHNICAL FIELD

This invention relates to intraocular lens inserters, and more specifically to guiding structures in the cartridges for intraocular lens inserters.

BACKGROUND

The techniques of cataract surgery are experiencing continuous, impressive progress. Subsequent generations of phacoemulsification platforms and newly invented surgical lasers keep increasing the precision of the placement of intraocular lenses (IOLs), and keep reducing the unwanted medical outcomes.

In a typical cataract procedure, an IOL is placed and folded into a cartridge, which is then placed into a tip of an inserter. Subsequently, a nozzle of the cartridge at the tip of the inserter is inserted into an eye through a surgically created incision, reaching the capsule of the eye. Then the IOL is pushed out of the cartridge through an insertion channel by a push-rod into the eye-capsule, where it is positioned, oriented, and rotated according to the pre-surgical plan, and then stabilized.

The more precisely the IOL is placed in the eye-capsule, the better the medical outcome. The precision placement of the IOL involves placing the IOL to the planned location with the planned orientation, as determined during the pre-surgical planning process. This is especially important for high-end toric, diffractive, and aspheric IOLs, whose optical axes need to be aligned with the planned orientation within a few degrees to achieve the planned and promised vision correction.

In a typical cataract procedure, in order to minimize the length of the incision, the insertion nozzle of the cartridge is tapered and its diameter is made as small as possible. To make the IOL able to pass through this narrow and tapered insertion nozzle, the IOL is folded up and compressed substantially when it is placed into the cartridge. The gain associated with the narrowness of the insertion nozzle and the shortness of the incision, however, comes at a price, as the heavily compressed IOL tends to rotate while it is pushed through the tapered nozzle. Because of this rotation, the orientation of the IOL, and its haptics, after insertion often deviates from the surgically planned orientation. This is an undesirable outcome that undermines the medical benefit of the cataract procedure, especially when involving advanced IOLs, such as toric, diffractive, and aspheric IOLs, and any other intraocular lens designs, for which the orientation of the IOL or its haptic is important. Therefore, there is a profound need to reduce and potentially eliminate the rotation of the IOL as it is pushed along the insertion nozzle.

SUMMARY

The above-described medical needs can be met by a cartridge of an intraocular lens inserter that comprises an insertion nozzle, having a distal insertion channel; an intraocular lens (IOL)-folding stage, to receive and to fold an IOL, proximal to the insertion nozzle, and having a proximal insertion channel; and an IOL-guiding structure. The IOL-guiding structure can include a first proximal guiding groove, or a first proximal guiding rib, or both, formed in the IOL-folding stage. In some embodiments, an intraocular lens inserter comprises an inserter cylinder; a push-rod, partially in the inserter cylinder; a cartridge-receiving insertion end, to receive a cartridge that includes an insertion nozzle, having a distal insertion channel; an IOL-folding stage, proximal to the insertion nozzle, having a proximal insertion channel; and an IOL-guiding structure.

DETAILED DESCRIPTION

This document describes embodiments of ophthalmic inserters and their cartridges that provide improvements regarding the above described medical needs.

Figure 1:
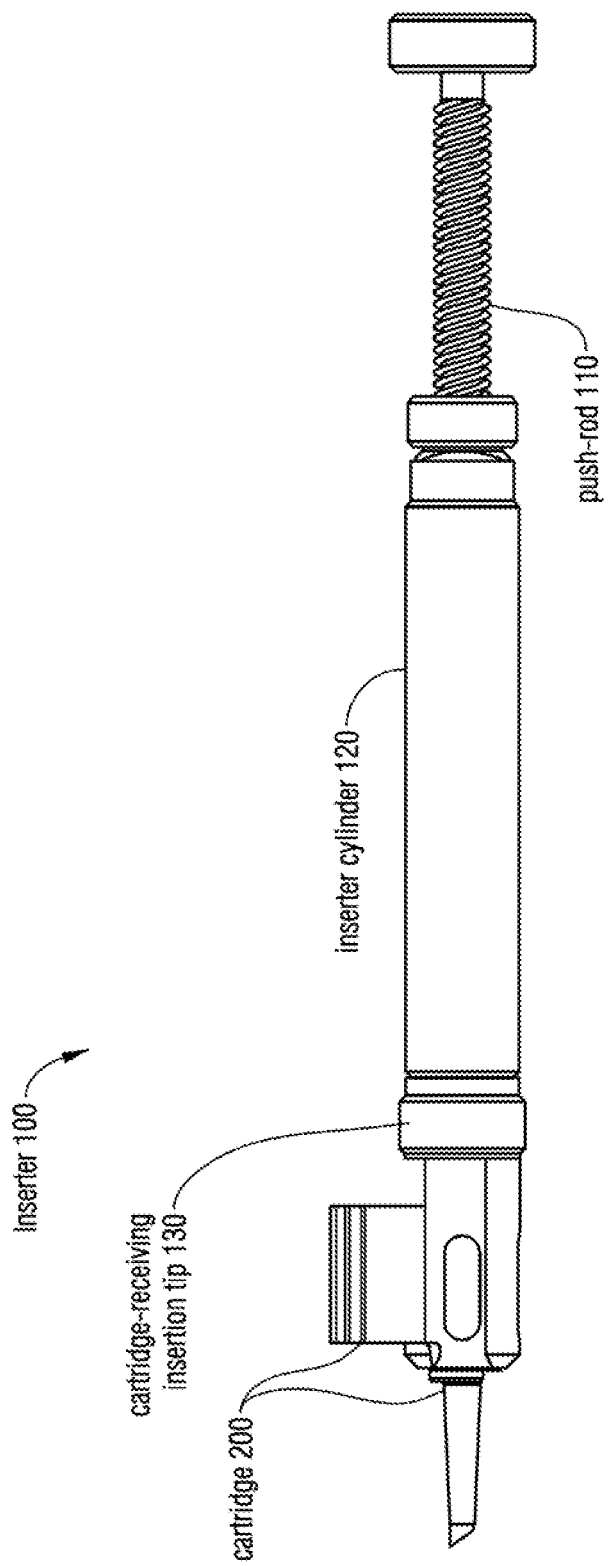
FIG. 1 illustrates an inserter 100.

FIG. 1 illustrates an inserter 100 for use in cataract surgeries to insert an intra-ocular lens (IOL) 10 into the capsule of an eye through an incision made by the surgeon. The main components of the inserter 100 include a push-rod 110, an inserter cylinder 120, and a cartridge-receiving tip 130. Some inserters 100 are re-usable, others are use-once disposable devices. Reusable inserters 100 can be made of titanium or other suitable metal, or plastic, and can be autoclavable.

Figure 2:
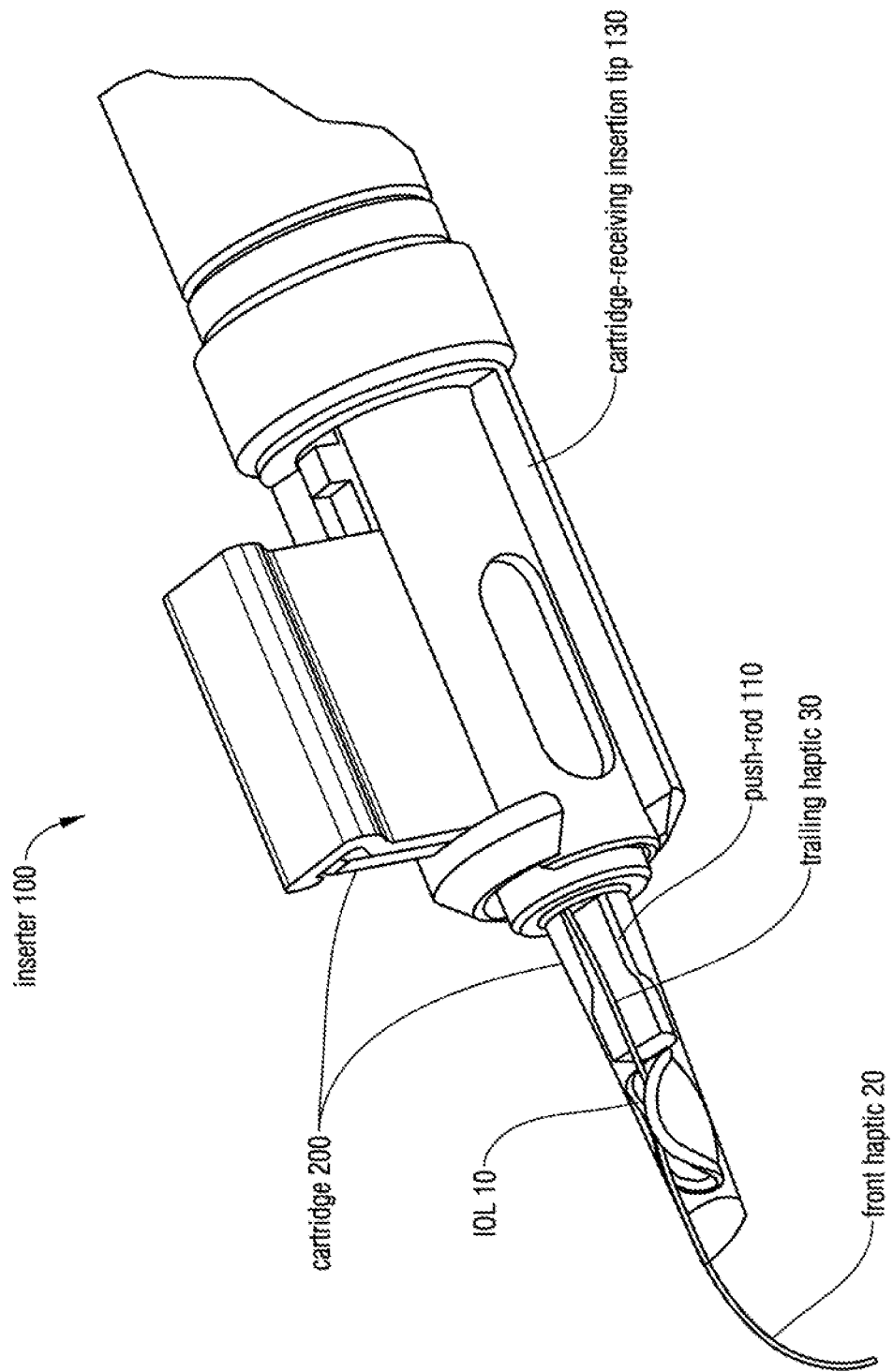
FIG. 2 illustrates an inserter 100 with a cartridge 200.
Figure 3:
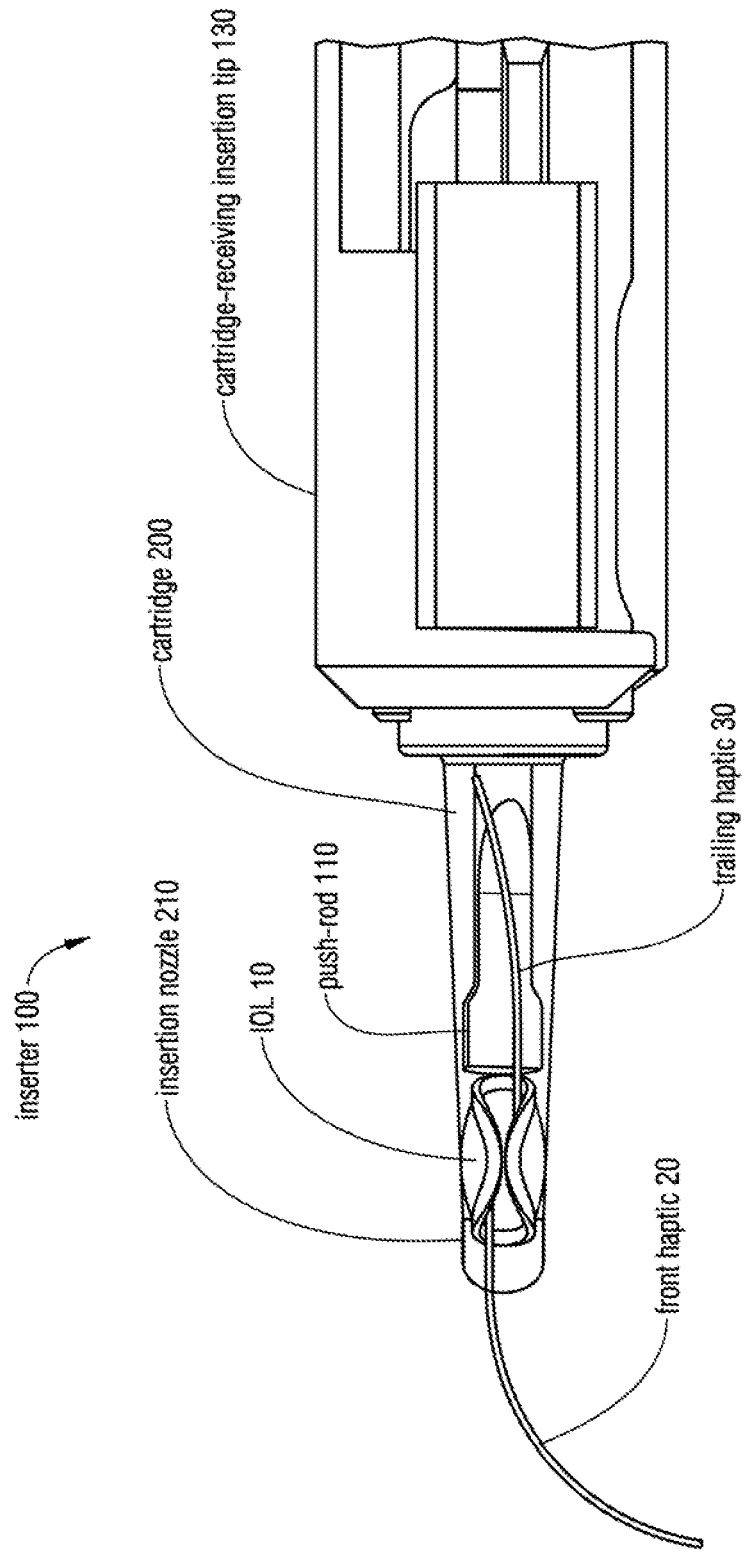
FIG. 3 illustrates an IOL 10 loaded into a cartridge 200.

A typical use of the inserter 100 can include the following steps. (1) The IOL 10 is placed, or loaded, and then folded into a cartridge 200. (2) The cartridge 200 is positioned into the cartridge-receiving tip 130 of the inserter 100. (3) A distal tip, or insertion nozzle, of the cartridge 200 is inserted into an eye through an incision, created earlier by the surgeon. (4) FIGS. 2 and 3 show that after the insertion of the distal tip of the cartridge 200 into the eye, the IOL 10 is pushed forward by advancing the push rod 110. The IOL 10 is eventually ejected from the cartridge 200 and thus gets inserted from the cartridge 200 into the eye. The push-rod 110 can be advanced by turning a screw, as shown, or by direct pushing, or by a variety of other known mechanical solutions. In some embodiments, the inserter cylinder 120 can be referred to as a main body, and the cartridge-receiving tip 130 can be referred to as, or include, a cover.

As discussed earlier, there are clear medical benefits associated with inserting the IOL 10 into the capsule of the eye with a preferred, or predetermined, alignment and orientation. It is noted that it is not sufficient to load the IOL 10 into the cartridge 200 with the planned orientation, because the IOL 10 can, and often does rotate away from its preferred orientation as it is pushed through the small diameter distal end of the cartridge 200 by the push rod 110. This can lead to undesirable medical outcomes, such as the misalignment of the major meridians of an implanted toric IOL with the axis of astigmatism of the eye. This issue is of substantial importance, as even a few degree misalignment of a toric lens from a planned direction can lead to substantial discomfort for the patient. It is a recurring event that even a seemingly small misalignment is so bothersome that some patients ask for a second procedure to rotate the IOL, or possibly even to remove the IOL from the eye altogether. Especially in "patient-pay" procedures that promise high quality outcomes, such a surgical result is highly undesirable.

Embodiments of the here-described cartridge 200 are designed to reduce, to restrain, to minimize and possibly to eliminate this undesirable IOL rotation during the insertion process.

FIGS. 4-9B illustrate embodiments of the cartridge 200 that include an insertion nozzle 210, having a distal insertion channel 220-*d*; an intraocular ophthalmic lens (IOL)-folding stage 230, proximal to the insertion nozzle 210, having a proximal insertion channel 220-*p*; and an IOL-guiding structure 240. In some detail, FIGS. 4-6 describe the structure of embodiments of the cartridge 200 from different perspectives, and FIGS. 7-9B illustrate the loading of the IOL 10 into the cartridge 200, and the insertion of the IOL 10 from different perspectives and at different stages. The below description focuses on the various embodiments and variants of the IOL-guiding structure 240.

Figure 4:
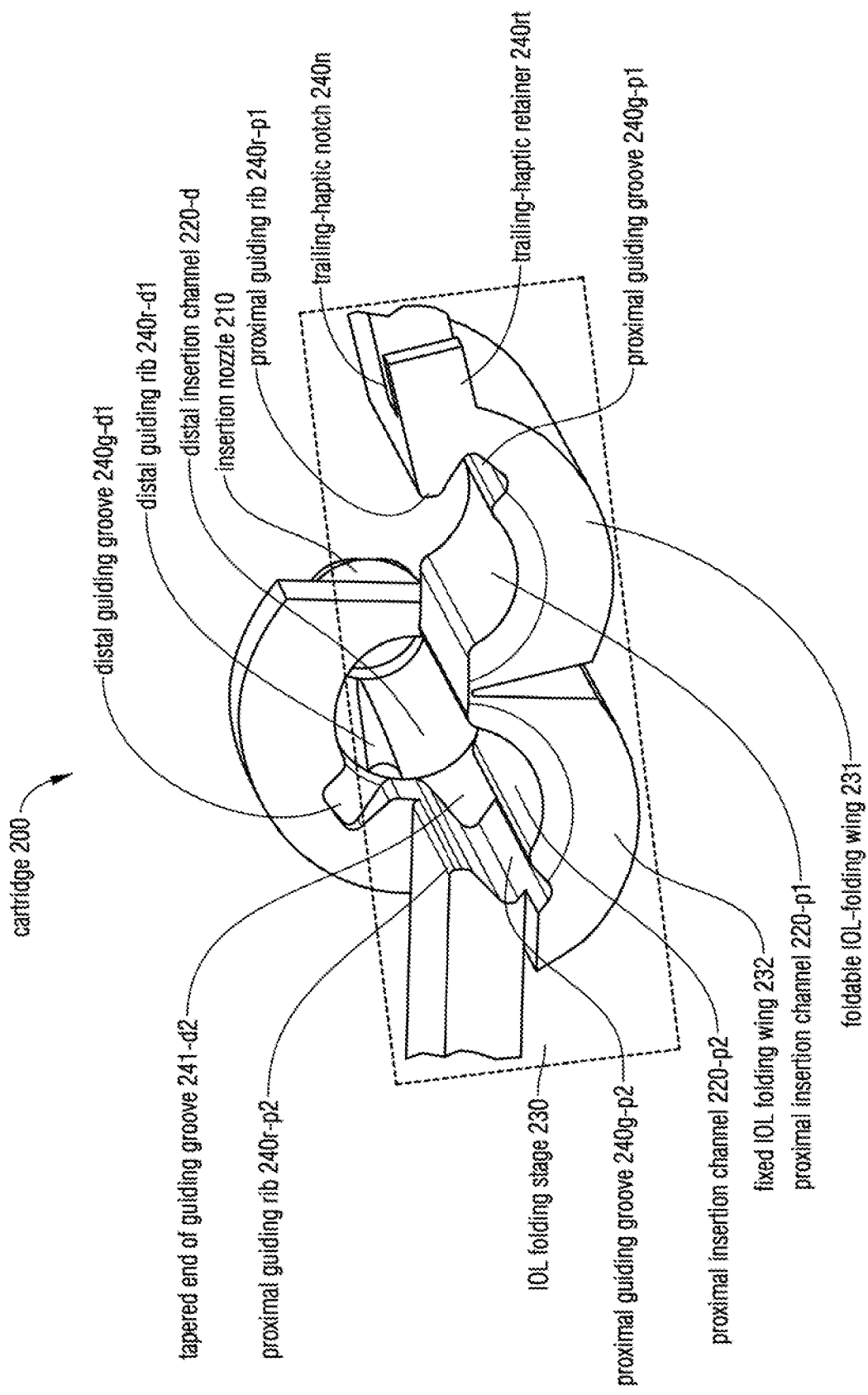
FIG. 4 illustrates a perspective view of a cartridge 200 from a proximal front.

FIG. 4 shows that in some embodiments, the IOL-guiding structure 240 can include a first proximal guiding groove 240*g*-*p*1, formed in the IOL-folding stage 230. This first proximal guiding groove 240*g*-*p*1 can guide the IOL 10 during its insertion and restrain its rotation, as described below in detail. In the description below, the labels "p" and "d" typically refer to an element being "proximal" or "distal". Further, in the Figures, the terms "first" and "second" are represented only by the added labels "1" and "2", respectively.

Figure 6:
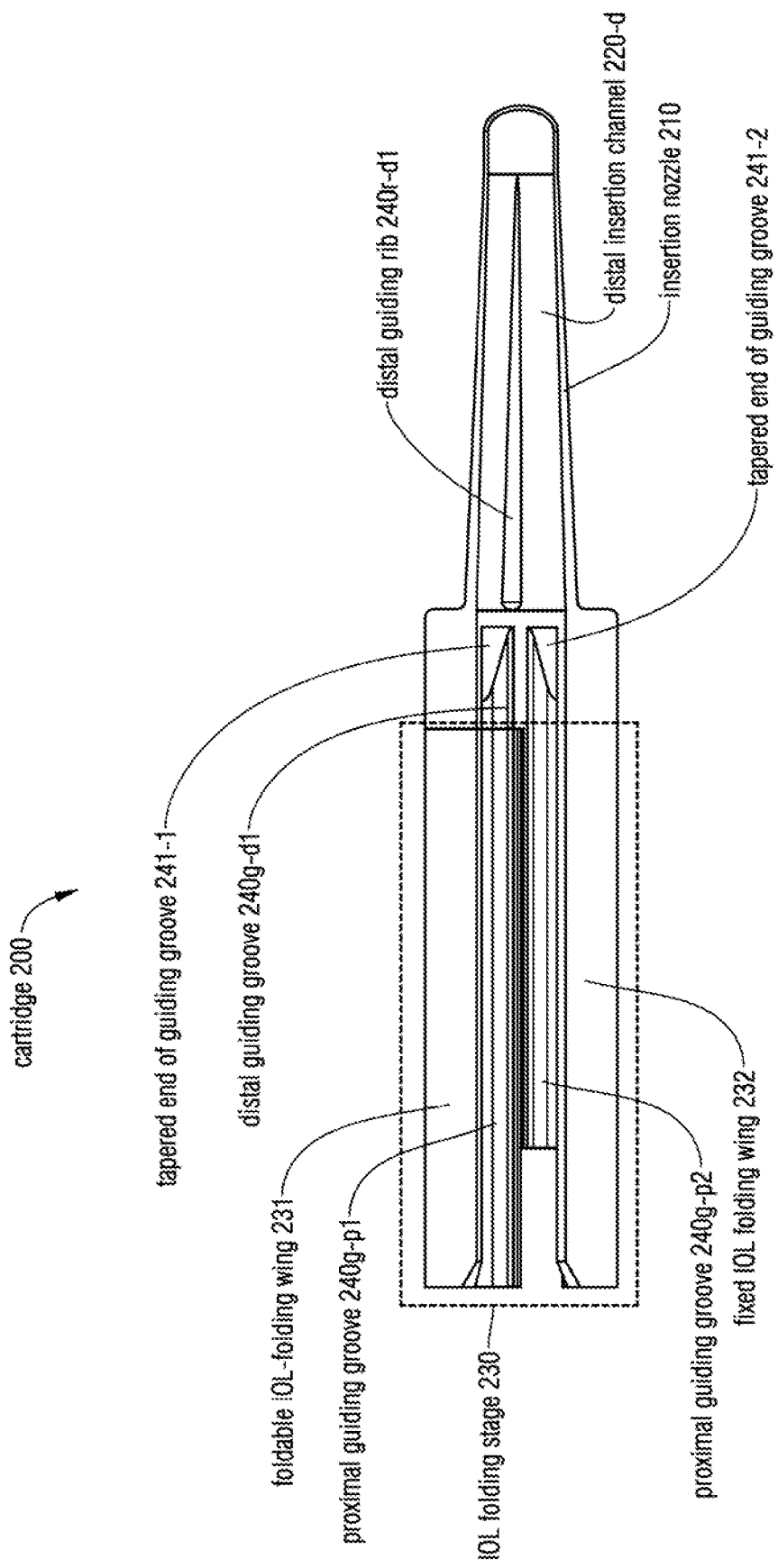
FIG. 6 illustrates a longitudinal cross section of a cartridge 200.

The IOL-guiding structure 240 can further include a second proximal guiding groove 240*g*-*p*2, also formed in the IOL folding stage 230, and a first distal guiding groove 240*g*-*d*1, formed distal to the IOL folding stage 230. In some embodiments, the first distal guiding groove 240*g*-*d*1 is formed as part of the insertion nozzle 210. In others, the first distal guiding groove 240*g*-*d*1 can be formed distal to the IOL folding stage 230, but proximal to the insertion nozzle 210, as shown in FIG. 6. The guiding grooves 240*g*-*d*1, 240*g*-*p*1 and 240*g*-*p*2 together will be referenced as guiding grooves 240*g*. Each of these guiding grooves can guide the IOL 10 during insertion, and restrain its rotation. While FIG. 4 only shows one distal guiding groove 240*g*-*d*1, some embodiments may include an additional distal guiding groove 240*g*-*d*2, not shown explicitly.

The IOL-folding stage 230 can include a foldable IOL-folding wing 231, to partially receive the IOL 10, and a fixed IOL-folding wing 232, to partially receive the IOL 10. In some embodiments, the first proximal guiding groove 240*g*-*p*1 can be formed in the foldable IOL-folding wing 231, in other embodiments, in the fixed IOL-folding wing 232, or partially in both. In the illustrated examples, the first proximal guiding groove 240*g*-*p*1 will be shown formed in the foldable IOL-folding wing 231, but the mirrored embodiments, in which the first proximal guiding groove 240*g*-*p*1 is formed in the fixed IOL-folding wing 232 are also used in other embodiments.

In embodiments that have both the first proximal guiding groove 240*g*-*p*1, and the second proximal guiding groove 240*g*-*p*2, the first proximal guiding groove 240*g*-*p*1 can be formed in the foldable IOL-folding wing 231, and the second proximal guiding groove 240*g*-*p*2 can be formed in the fixed IOL-folding wing 232, so that both IOL-folding wings 231 and 232 have a proximal guiding groove 240*g*-*p*1 or 240*g*-*p*2. The fixed IOL-folding wing 232 can be fixed relative to the insertion nozzle 210.

FIGS. 4, 5B, and 9A-B show that in some embodiments, the proximal insertion channel 220-*p* is formed or defined by a first proximal insertion channel 220-*p*1 in the foldable IOL-folding wing 231 and by a second proximal insertion channel 220-*p*2 in the fixed IOL-folding wing 232, when the foldable IOL-folding wing 231 is clasped or attached to the fixed IOL-folding wing 232 with a clasp 270.

Figure 7:
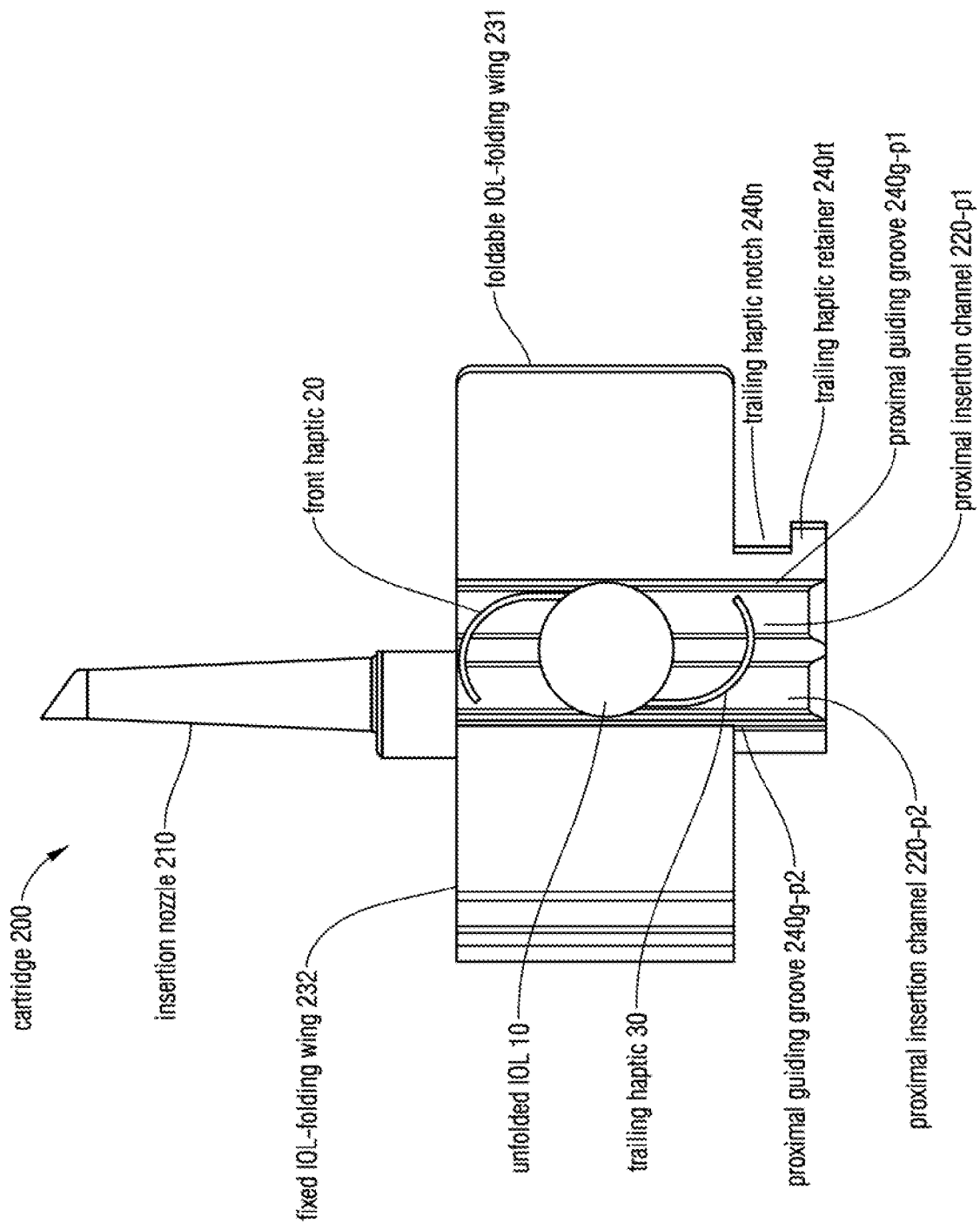
FIG. 7 illustrates an open cartridge 200 with an IOL 10 loaded.

FIG. 7 illustrates that when the IOL 10 is loaded into the cartridge 200, it is positioned onto the foldable IOL-folding wing 231 and onto the fixed IOL-folding wing 232, over the first and second proximal insertion channels 220-*p*1 and 220-*p*2. The foldable IOL-folding wing 231 and the fixed IOL-folding wing 232 are in this sense configured to partially receive the IOL 10.

A leading function of the guiding grooves 240*g* is to guide the IOL 10 during insertion, thus restraining and reducing an unintended rotation of the IOL 10. In some detail, the first proximal guiding groove 240*g*-*p*1 can be configured to catch an edge of the IOL 10 and then guide this edge during the insertion of the IOL 10, thereby restraining a rotation of the IOL 10 as it moves along the proximal insertion channel 220-*p*. To make the guiding firmer, embodiments of the cartridge 200 may include the second proximal guiding groove 240*g*-*p*2 that catches an opposite edge of the IOL 10. Such embodiments of the cartridge 200 can provide a firmer guidance and constrain the IOL 10 more efficiently from rotating during insertion. Some embodiments of the guiding grooves 240*g* can reduce, restrain, or constrain the rotation of the IOL 10 particularly efficiently. These embodiments can minimize and even prevent a rotation of the IOL 10 during insertion. The IOL 10 being round, an edge of the IOL 10 typically refers to a short first segment of the circular perimeter of the IOL 10, and an opposite edge can refer to a short second segment that is diagonally opposite to the first segment.

Figure 8:
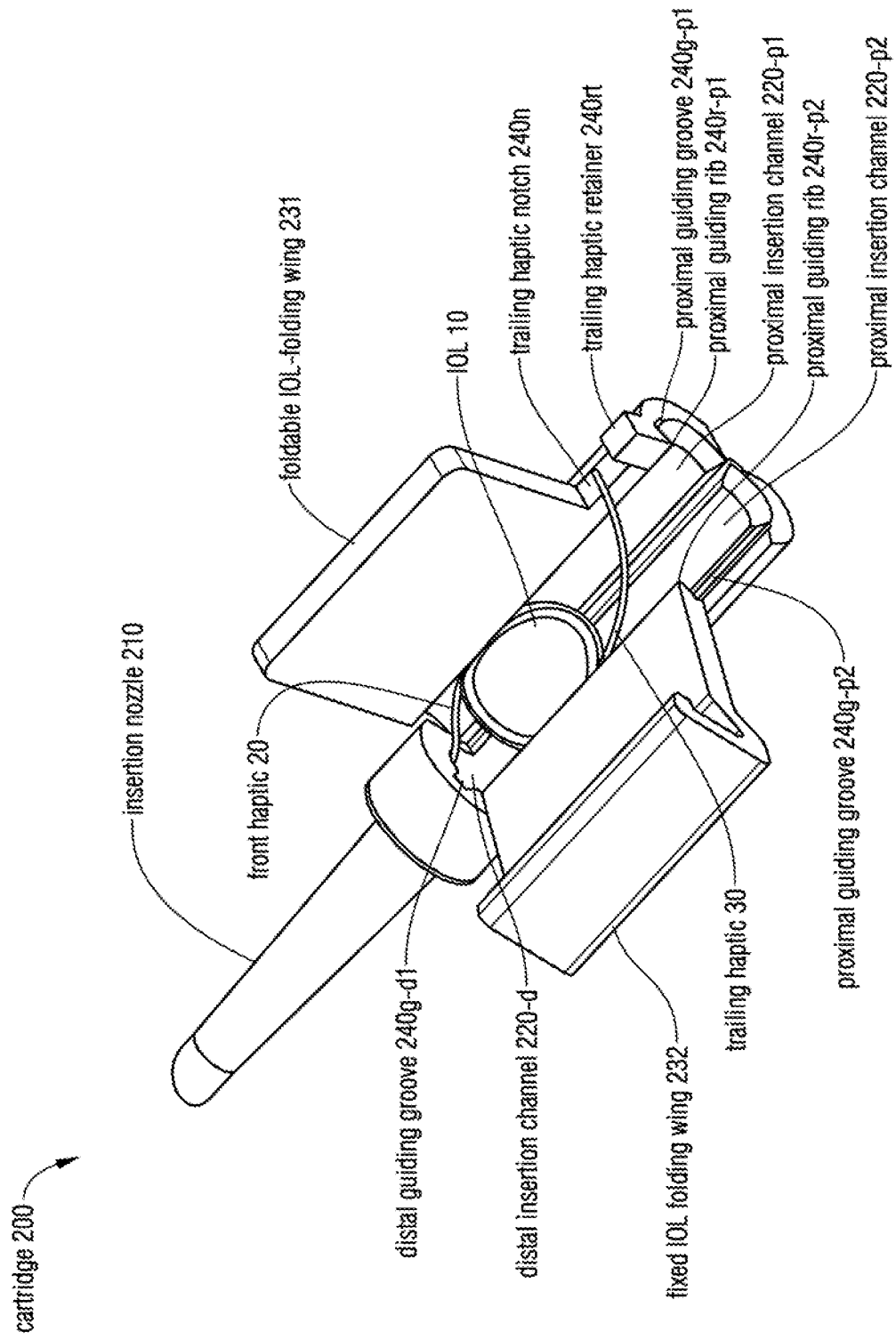
FIG. 8 illustrates a cartridge 200 with an IOL 10 during the folding process.
Figure 9A:
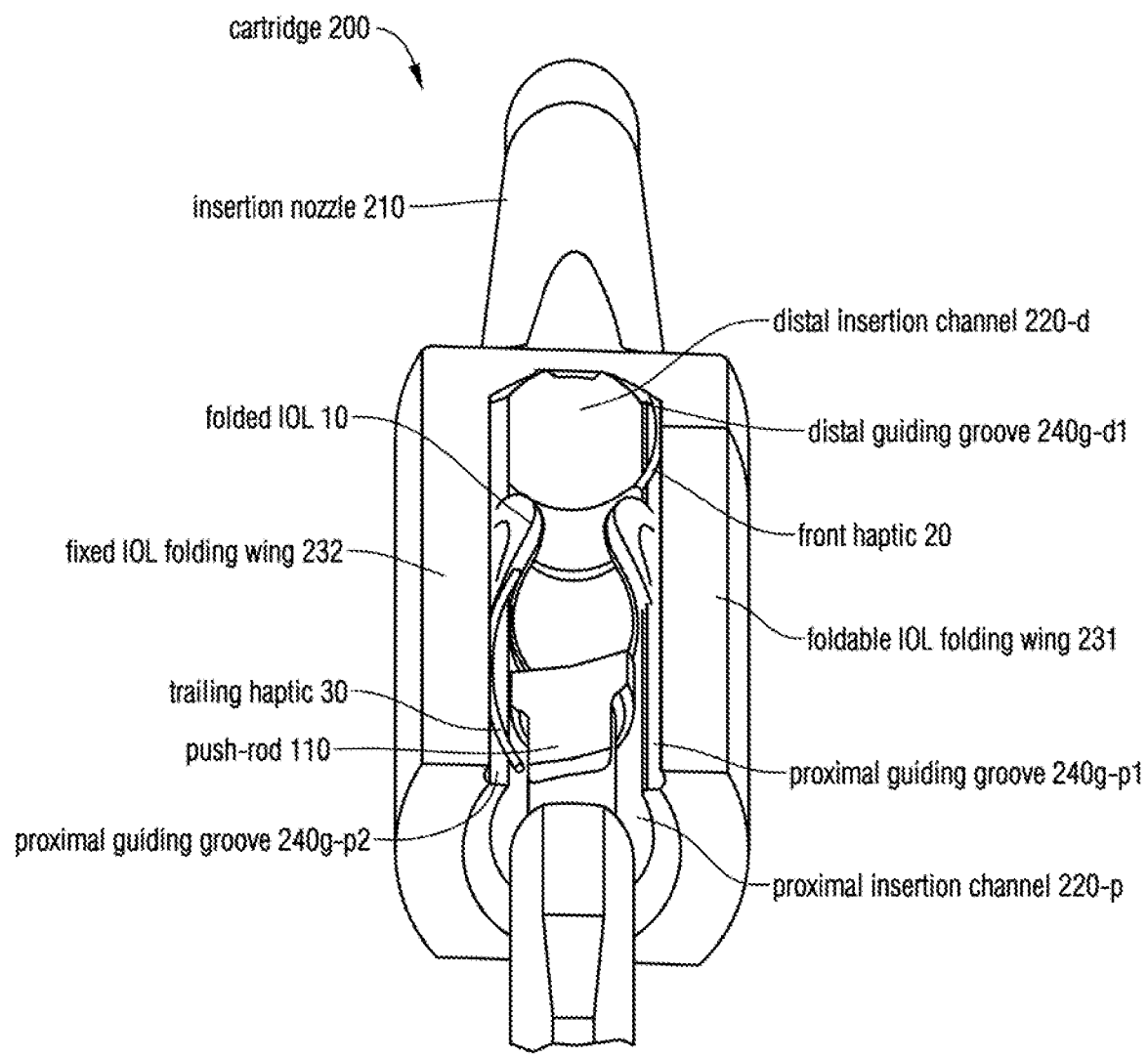
FIGS. 9A-B illustrate a cartridge 200 with a folded IOL 10, pushed by a push-rod 110.

FIGS. 7-9A illustrate that the proximal guiding grooves 240*g*-*p* (referring to the first and second proximal guiding grooves 240*g*-*p*1 and 240*g*-*p*2) can have more than one function. In some embodiments, the first proximal guiding groove 240*g*-*p*1, or the second proximal guiding groove 240*g*-*p*2, or both, can be configured to also help folding the IOL 10 by catching an edge of the IOL 10 as part of the folding process. Indeed, in some typical cases, the loading of the IOL 10 can start with simply placing the IOL 10 on, or over, the two semi-cylinders of the first and second proximal insertion channels 220-*p*1 and 220-*p*2. Then, an operator can start folding the foldable IOL-folding wing 231. Without a mechanical constraint, or restraining force, the IOL 10 may pop out, or slide out, from the proximal insertion channels 220-*p*1 and 220-*p*2, preventing the controlled folding of the IOL 10. This challenge can be brought under control by the proximal guiding groove 240*g*-*p*1, or 240*g*-*p*2, or both, catching an edge of the IOL 10, and thus preventing a pop-out, or slide-out, thereby enabling a well-controlled folding of the IOL 10. An initial stage of the IOL folding is shown in FIG. 7, an intermediate stage of the folding is shown in FIG. 8, and the end of the folding is shown in FIG. 9A.

FIG. 6 illustrates that some of the embodiments of the cartridge 200 can also have a first distal guiding groove, 240*g*-*d*1. The first distal guiding groove 240*g*-*d*1 can be formed distally to the IOL folding stage 230. The first distal guiding groove 240*g*-*d*1 is sometimes formed in the insertion nozzle 210. FIG. 6 shows that in some other designs, the cartridge 200 may include a short intermediate segment, distal to the IOL-folding stage 230, but proximal to the insertion nozzle 210. In such designs, the first distal guiding groove 240g-d1 can be formed in this intermediate segment, essentially as a continuation of the first proximal guiding groove 240g-p1. The first distal guiding groove 240g-d1 can be configured to guide an edge of the IOL 10 during an insertion of the IOL into an eye, thereby restraining a rotation of the IOL 10 as it moves along the distal insertion channel 220-d.

In some designs, the second proximal guiding groove 240g-p2, that is formed in the fixed IOL folding wing 232, can be longer than the first proximal guiding groove 240g-p1. In the embodiment of FIG. 6, the second proximal guiding groove 240g-p2 is as long as the first proximal guiding groove 240g-p1 and the corresponding first distal guiding groove 240g-d1 combined. The end-portion of the second proximal guiding groove 240g-p2, parallel with the first distal guiding groove 240g-d1 can be nominally called a second distal guiding groove 240g-d2, but structurally, this end-portion is simply a continuation of the second proximal guiding groove 240g-p2 in some embodiments.

In some embodiments, the first distal guiding groove 240g-d1 can be aligned with the first proximal guiding groove 240g-p1. In such embodiments, the guided edge of the IOL 10 can smoothly pass from the first proximal guiding groove 240g-p1 to the first distal guiding groove 240g-d1 as the push-rod 110 advances the IOL 10 from the proximal insertion channel 220-p into the distal insertion channel 220-d.

FIG. 6 also illustrates that the guiding grooves can end in a tapered manner, since the entire IOL 10 needs to get compressed as it advances toward the narrower and tapered insertion nozzle 210 during insertion. The aligned first guiding grooves 240g-p1/240g-d1 can end with a tapered end of the guiding groove 241-1, and the second proximal guiding groove 240g-p2 can end with a tapered end of guiding groove 241-2. The second proximal guiding groove 240g-p2 can extend beyond the IOL folding stage 230, so that its tapered end 241-2 can align with the tapered end 241-1 of the aligned first guiding grooves 240g-p1/240g-d1. One of the reasons for the tapered design is that the insertion nozzle 210 itself can be tapered, its outer diameter decreasing to smaller and smaller values towards its distal tip, so that it can fit into the incision made by the surgeon. In typical cataract surgeries, the incision can be 2.5-3 mm long and accordingly the outer diameter of the distal tip of the insertion nozzle 210 can be reduced to the range of 1-3 mm. In some embodiments, the outer diameter of the insertion nozzle can be in the 1-2 mm range.

Figure 9B:
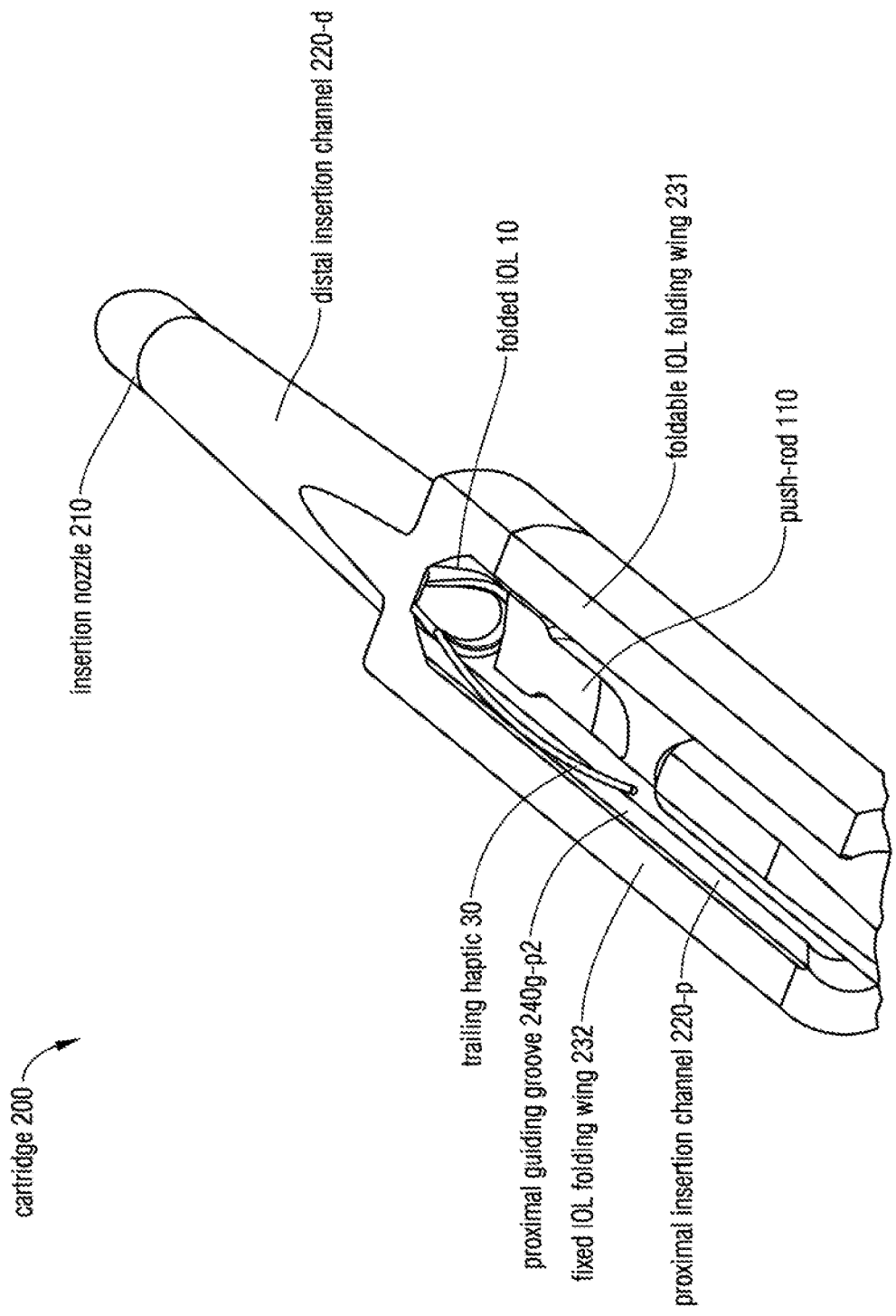

FIGS. 9A-B illustrate an early stage and a later stage of the insertion of the IOL 10. FIG. 9A shows a folded IOL 10 inside the IOL-folding stage 230 of the cartridge 200 after the folding has been completed. For clarity, in this cut-away drawing, only the inner walls of the cartridge 200 are shown, forming the proximal insertion channel 220-p and the distal insertion channel 220-d. FIG. 9A shows the stage of the IOL insertion when the push-rod 110 is pushing the IOL 10 from the proximal insertion channel 220-p into the distal insertion channel 220-d. FIG. 9B shows the stage when the IOL 10 has been largely pushed into the distal insertion channel 220-d. Visibly, the guiding grooves 240g managed to reduce and constrain the rotation of the IOL 10 during these stages of the insertion.

Figure 5A:
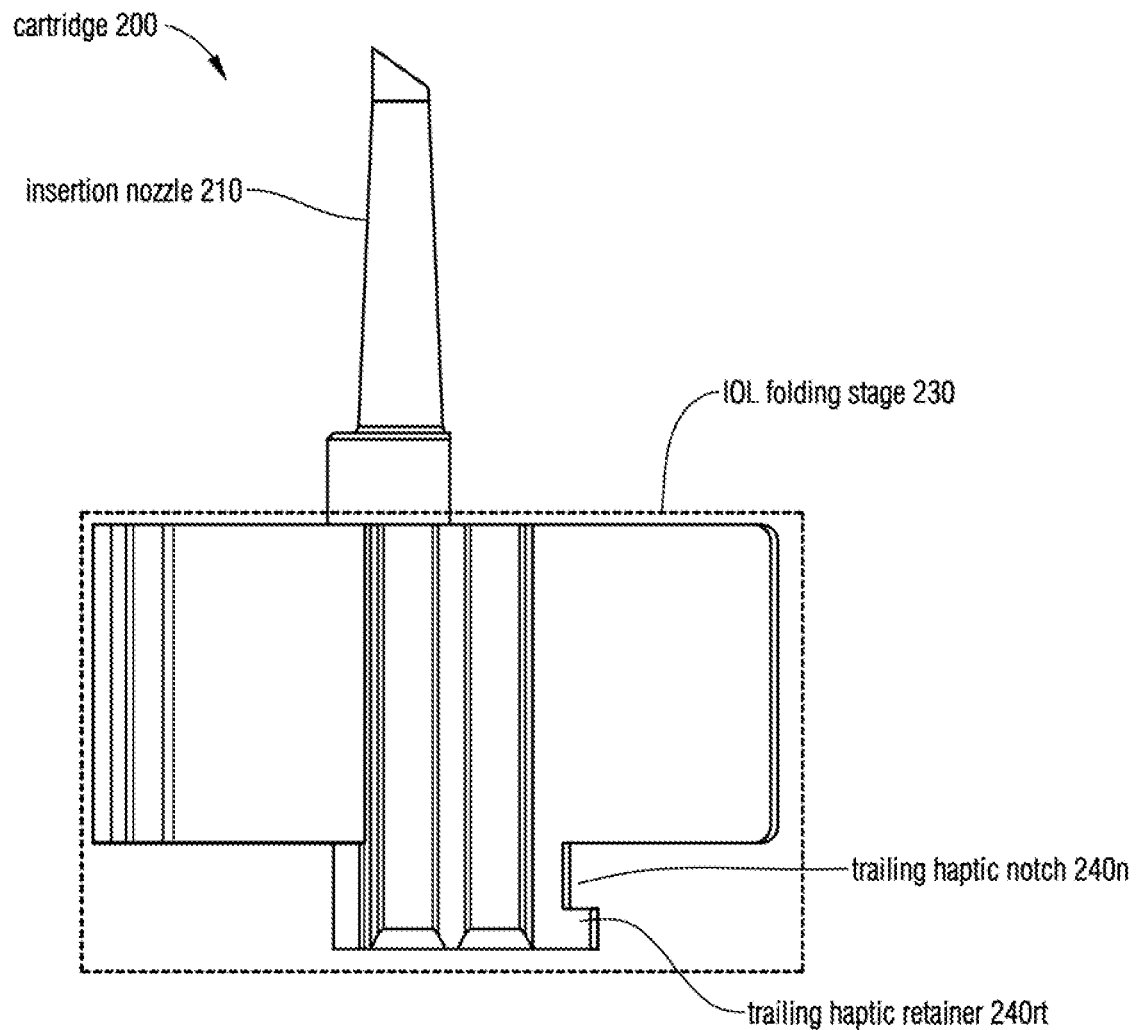
FIGS. 5A-B illustrate perspective views of a cartridge 200.
Figure 5B:
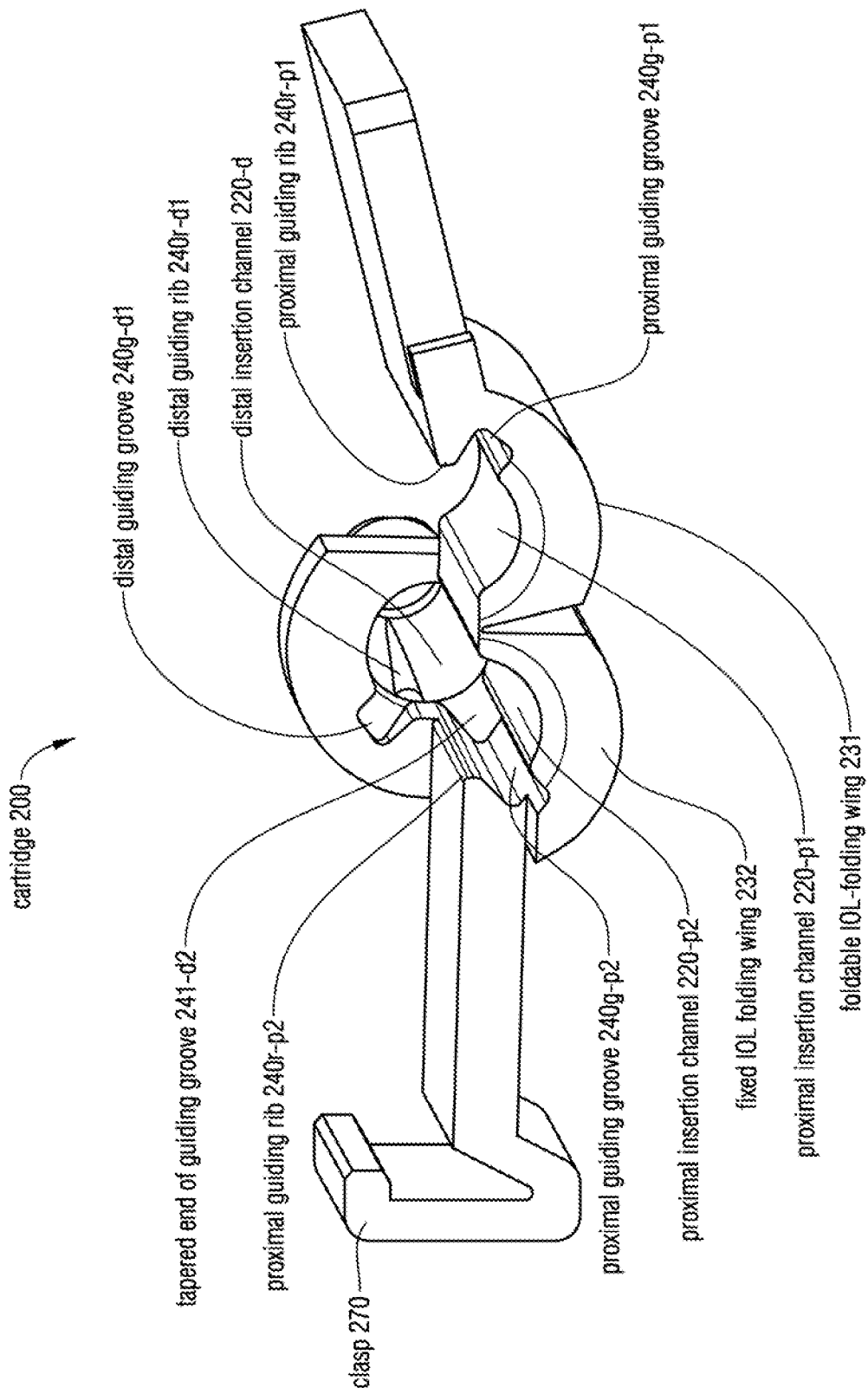

Next, another embodiment of the IOL-guiding structure 240 will be described. FIGS. 4 and 5B illustrate that in some embodiments, the IOL-guiding structure 240 can include a first proximal guiding rib 240r-p1, formed in the IOL-folding stage 230, to protrude into the proximal insertion channel 220-p.

As before, in some embodiments, the IOL-folding stage 230 can include the foldable IOL-folding wing 231, to partially receive the IOL 10, and the fixed IOL-folding wing 232, to partially receive the IOL 10. In some embodiments, the first proximal guiding rib 240r-p1 can be formed in the foldable IOL-folding wing 231. In others, the first proximal guiding rib 240r-p1 can be formed in the fixed IOL-folding wing 232. In the illustrated examples, the first proximal guiding rib 240r-p1 will be shown formed in the foldable IOL-folding wing 231, but the mirrored embodiments, in which the first proximal guiding rib 240r-p1 is formed in the fixed IOL-folding wing 232 are also used in other embodiments.

As shown in FIG. 5B, the foldable IOL-folding wing 231 and the fixed IOL-folding wing 232 can form the proximal insertion channel 220-p when the foldable IOL-folding wing 231 is clasped or attached to the fixed IOL-folding wing 232 with clasp 270.

Some embodiments can include two proximal guiding ribs 240r-p: the first proximal guiding rib 240r-p1, formed in the foldable IOL-folding wing 231, and a second proximal guiding rib 240r-p2, formed in the fixed IOL-folding wing 232, so that both IOL-folding wings 231 and 232 have a proximal guiding rib 240r-p1 and 240r-p2.

FIG. 5B and FIG. 6 illustrate that some embodiments of the cartridge 200 can also include a first distal guiding rib 240r-d1, formed distally from the IOL-folding stage 230. In some embodiments, the first distal guiding rib 240r-d1 can be formed distally to the IOL folding stage 230. In the embodiment of FIG. 6, the first distal guiding rib 240r-d1 is firmed in the insertion nozzle 210. FIG. 6 shows that in some other designs, the cartridge 200 may include a short intermediate segment, distal to the IOL-folding stage 230, but proximal to the insertion nozzle 210. In some designs, not shown, the first distal guiding rib 240r-d1 can be at least partially formed in this intermediate segment. The first distal guiding rib 240r-d1 can be configured to guide an edge of the IOL 10 during an insertion of the IOL into the eye, thereby restraining a rotation of the IOL 10 as it moves along the distal insertion channel 220-d. While FIG. 5B and FIG. 6 only show one distal guiding rib 240r-d1, some embodiments may include an additional distal guiding rib 240r-d2, not shown explicitly.

A leading function of the guiding ribs 240r-p1, 240r-p2, and 240r-d1 is to guide an edge of the IOL 10 during insertion. In some detail, the guiding ribs 240r-p1, 240r-p2, and 240r-d1 can be configured to protrude into the proximal insertion channel 220-p, and into the distal insertion channel 220-d to guide an edge of the IOL 10 during the IOL insertion, thereby reducing and restraining a rotation of the IOL 10 as it is pushed forward by the push rod 110 during insertion.

FIG. 8 illustrates that in some embodiments, the proximal guiding ribs 240r-p1 and 240r-p2 can have the additional function of helping the folding of the IOL 10 by catching an edge of the IOL 10 as part of the folding process. As before, FIG. 7 shows the beginning of the process of folding the IOL 10, when the flat IOL 10 is placed on the foldable IOL-folding wing 231 and the fixed IOL-folding wing 232, both partially receiving the IOL 10. FIG. 8 illustrates an intermediate stage of the folding, where the first and second proximal guiding ribs 240r-p1 and 240r-p2 each caught an edge of the IOL 10, and thus control the folding of the IOL 10 as the foldable IOL-folding wing 231 is folded in. FIG. 9A illustrates the advanced folding stage when the IOL 10 has been completely folded.

In embodiments that include both the first proximal guiding rib 240r-p1 and the first distal guiding rib 240r-d1, the first distal guiding rib 240r-d1 can be aligned with the first proximal guiding rib 240r-p1. In such embodiments, the caught edge of the IOL 10 can smoothly pass from the first proximal guiding rib 240r-p1 to the first distal guiding rib 240r-d1 as the push-rod 110 advances the IOL 10 from the proximal insertion channel 220-p to the distal insertion channel 220-d.

FIG. 6 illustrates that in some other embodiments that include both the first proximal guiding rib 240r-p1 and the first distal guiding rib 240r-d1, the first distal guiding rib 240r-d1 may not be aligned with the first proximal guiding rib 240r-p1. In such embodiments, the caught edge of the IOL 10 turns with a predetermined, preferred angle as it passes from the first proximal guiding rib 240r-p1 to the first distal guiding rib 240r-d1 as the push-rod 110 advances the IOL 10 from the proximal insertion channel 220-p to the distal insertion channel 220-d. This planned rotation of the IOL 10 may be dictated, or preferred, by mechanical considerations of the insertion process, or by medical considerations, to make the IOL 10 reach its most preferred orientation.

FIG. 6 illustrates that the first distal guiding rib 240r-d1 can be tapered, ending part way in the insertion nozzle 210. As before, one reason for this design can be that the entire insertion nozzle 210 is tapered, thus it is beneficial to reduce and phase out the protruding first distal guiding rib 240r-d1 as the IOL 10 gets ever more compressed in the ever more cramped space of the tapered insertion nozzle 210.

Finally, the IOL-guiding structure 240 can have other embodiments that combine the above designs. These embodiments may include one or more guiding grooves 240g-p1, 240g-p2, and 240g-d1, and one or more guiding ribs 240r-p1, 240r-p2, and 240r-d1 in various combinations. Having both guiding grooves 240g and guiding ribs 240r can make the overall IOL-guiding structure 240 more efficient in achieving its main function of reducing or controlling the rotation of the IOL 10 during insertion, as well as achieving its additional functions, such as assisting the IOL folding process.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to another subcombination or a variation of a subcombinations.

The invention claimed is:

1. A cartridge of an intraocular lens inserter, comprising: an insertion nozzle, having a distal insertion channel; an intra-ocular lens (IOL)-folding stage, to receive and to fold an IOL, proximal to the insertion nozzle, and having a proximal insertion channel; and an IOL-guiding structure, including a first proximal guiding rib, formed in the IOL-folding stage to protrude into the proximal insertion channel, and a first protruding distal guiding rib, formed distal to the IOL folding stage, to protrude into the distal insertion channel, wherein the first distal guiding rib is not aligned with the first proximal guiding rib when the IOL-folding stage is clasped closed, and the distal insertion channel does not have a groove, formed beyond a circular cross-section of the distal insertion channel, wherein the first protruding distal guiding rib is formed in a tapered section of the distal insertion channel.

2. The cartridge of claim 1, the IOL-guiding structure comprising:
a first proximal guiding groove, formed in the IOL-folding stage.

3. The cartridge of claim 2, the IOL-folding stage comprising:
a fixed IOL-folding wing, to partially receive the IOL; and
a foldable IOL-folding wing, to partially receive the IOL, wherein
the first proximal guiding groove is formed in at least one of the fixed IOL-folding wing and the foldable IOL-folding wing.

4. The cartridge of claim 3, wherein:
the fixed IOL-folding wing and the foldable IOL-folding wing form the proximal insertion channel when the foldable IOL-folding wing is attached to the fixed IOL-folding wing.

5. The cartridge of claim 2, wherein:
the first proximal guiding groove is configured to guide an edge of the IOL during an insertion of the IOL into an eye, thereby restraining a rotation of the IOL as it moves along the proximal insertion channel.

6. The cartridge of claim 2, wherein:
the first proximal guiding groove is configured to catch an edge of the IOL as part of a folding of the IOL.

7. The cartridge of claim 3, comprising:
a second proximal guiding groove, formed so that the fixed IOL-folding wing has the second proximal guiding groove and the foldable IOL-folding wing has the first proximal guiding groove.

8. The cartridge of claim 1, the IOL-folding stage comprising:
a fixed IOL-folding wing, to partially receive the IOL; and
a foldable IOL-folding wing, to partially receive the IOL, wherein
the first proximal guiding rib is formed in at least one of the fixed IOL-folding wing and the foldable IOL-folding wing.

9. The cartridge of claim 8, wherein:
the fixed IOL-folding wing and the foldable IOL-folding wing form the proximal insertion channel when the foldable IOL-folding wing is attached to the fixed IOL-folding wing.

10. The cartridge of claim 8, comprising:
a second proximal guiding rib, formed so that the fixed IOL-folding wing has the second proximal guiding rib and the foldable IOL-folding wing has the first proximal guiding rib.

11. The cartridge of claim 1, wherein:
the first proximal guiding rib is configured to guide an edge of the IOL during an insertion of the IOL into an eye, thereby restraining a rotation of the IOL as it moves along the proximal insertion channel.

12. The cartridge of claim 1, wherein:
the first proximal guiding rib is configured to catch an edge of the IOL as part of a folding of the IOL.

13. The cartridge of claim 1, wherein:
the first distal guiding rib is configured to guide an edge of the IOL during an insertion of the IOL into an eye, thereby restraining a rotation of the IOL as it moves along the distal insertion channel.

14. An intraocular lens inserter, comprising: an inserter cylinder; a push-rod, partially in the inserter cylinder; a cartridge-receiving insertion end, to receive a cartridge that includes an insertion nozzle, having a distal insertion channel; an intraocular ophthalmic lens (IOL)-folding stage, to receive and to fold an IOL, proximal to the insertion nozzle, and having a proximal insertion channel; and an IOL-guiding structure, including a first proximal guiding rib, formed in the IOL-folding stage to protrude into the proximal insertion channel, and a first protruding distal guiding rib, formed distal to the IOL folding stage, to protrude into the distal insertion channel, wherein the first distal guiding rib is not aligned with the first proximal guiding rib when the IOL-folding stage is clasped closed, and the distal insertion channel does not have a groove, formed beyond a circular cross-section of the distal insertion channel, wherein the first protruding distal guiding rib is formed in a tapered section of the distal insertion channel.

\* \* \* \* \*